US006257886B1

(12) United States Patent
Warner

(10) Patent No.: US 6,257,886 B1
(45) Date of Patent: Jul. 10, 2001

(54) DISPOSABLE DENTAL PROPHYLAXIS ANGLE

(76) Inventor: Thomas P. Warner, 3704 Meriweather La., Rochester Hills, MI (US) 48306

( * ) Notice: Subject to any disclaimer, the term of this patent is extended or adjusted under 35 U.S.C. 154(b) by 0 days.

(21) Appl. No.: 09/338,831

(22) Filed: Jun. 23, 1999

Related U.S. Application Data
(60) Provisional application No. 60/090,335, filed on Jun. 23, 1998.

(51) Int. Cl.$^7$ .................................................. A61C 3/06
(52) U.S. Cl. ............................... 433/125; 433/82; 433/83
(58) Field of Search ......................... 433/125, 82, 83, 433/85, 87

(56) References Cited

U.S. PATENT DOCUMENTS

| | | | |
|---|---|---|---|
| 2,300,828 | 11/1942 | Goldenberg | 32/59 |
| 2,400,912 | * 5/1946 | Britt et al. | 433/125 X |
| 2,707,329 | 5/1955 | Costoff | 32/48 |
| 2,738,528 | 3/1956 | Fridge, Sr. | 15/97 |
| 3,389,468 | * 6/1968 | Lewis et al. | 433/82 X |
| 3,691,636 | 9/1972 | Deuschle | 32/58 |
| 3,727,313 | 4/1973 | Graham | 32/27 |
| 3,769,707 | 11/1973 | Condon | 32/27 |
| 3,775,849 | 12/1973 | Condon | 32/59 |
| 3,977,083 | * 8/1976 | Leslie et al. | 433/82 |
| 4,220,446 | * 9/1980 | Walker | 433/87 X |
| 4,259,071 | 3/1981 | Warden et al. | 433/166 |
| 4,266,933 | 5/1981 | Warden et al. | 433/82 |
| 5,062,796 | 11/1991 | Rosenberg | 433/82 |
| 5,209,658 | 5/1993 | Brahler | 433/125 |
| 5,360,339 | 11/1994 | Rosenberg | 433/165 |
| 5,374,189 | 12/1994 | Mendoza | 433/125 |
| 5,380,202 | 1/1995 | Brahler | 433/166 |
| 5,626,473 | 5/1997 | Muhlbauer et al. | 433/89 |
| 5,642,994 | * 7/1997 | Chipian et al. | 433/82 |
| 5,642,995 | 7/1997 | Bailey | 433/115 |
| 5,645,426 | 7/1997 | Grim et al. | 433/125 |
| 5,683,247 | 11/1997 | Bailey | 433/104 |
| 5,690,488 | 11/1997 | Spinello | 433/116 |

(List continued on next page.)

Primary Examiner—Nicholas D. Lucchesi
(74) Attorney, Agent, or Firm—Bliss McGlynn, P.C.

(57) ABSTRACT

A disposable dental prophylaxis angle including an elongated housing which defines a longitudinal axis and has a central bore and a head portion in fluid communication with the central bore. A prophylaxis cup is rotatably supported by the head portion and in fluid communication with the central bore through the head portion. An actuator is movably supported by the housing and includes a piston cooperatively received and supported in the central bore. Together, the piston and the central bore define a fluid chamber of decreasable volume located therebetween. A flowable dentifrice material may be contained within this chamber. The actuator is manually movable in the direction of the longitudinal axis of the housing to move the piston within the central bore in an indexing fashion in successive increments of a predetermined distance therealong, to reduce the volume of the chamber and to force the flowable dentifrice material in predetermined, incremental amounts which correspond to the distance traveled by the piston, from the chamber to the prophy cup via the head portion. In addition, the present invention discloses an actuator including a cam and a push rod having a cam follower, an isolation tube and a piston which is movably supported on the isolation tube in one direction but which allows relative movement of the isolation tube in the opposite direction to advance the dentifrice material from the chamber to the prophy cup. In addition, the present invention includes a primary drive gear having flow paths which promote the flow of the dentifrice material therethrough when rotated in one direction. Finally, the present invention also incorporates a paste delivery system having a dentifrice dispensing nipple formed on the head portion of the housing.

40 Claims, 8 Drawing Sheets

U.S. PATENT DOCUMENTS

| | | | |
|---|---|---|---|
| 5,692,901 | 12/1997 | Roth et al. | 433/85 |
| 5,707,234 | 1/1998 | Bender | 433/90 |
| 5,718,582 | 2/1998 | Quinn et al. | 433/127 |
| 5,730,593 | 3/1998 | Mack | 433/60 |
| 5,730,595 | 3/1998 | Bailey | 433/125 |
| 5,749,728 | 5/1998 | Bailey | 433/125 |
| 5,775,905 | 7/1998 | Weissenfluh et al. | 433/166 |
| 5,797,744 | 8/1998 | Rosenberg | 433/166 |
| 5,871,353 * | 2/1999 | Pierce et al. | 433/125 X |
| 5,876,203 | 3/1999 | Bailey | 433/104 |
| 5,902,107 | 5/1999 | Lowell | 433/130 |

* cited by examiner

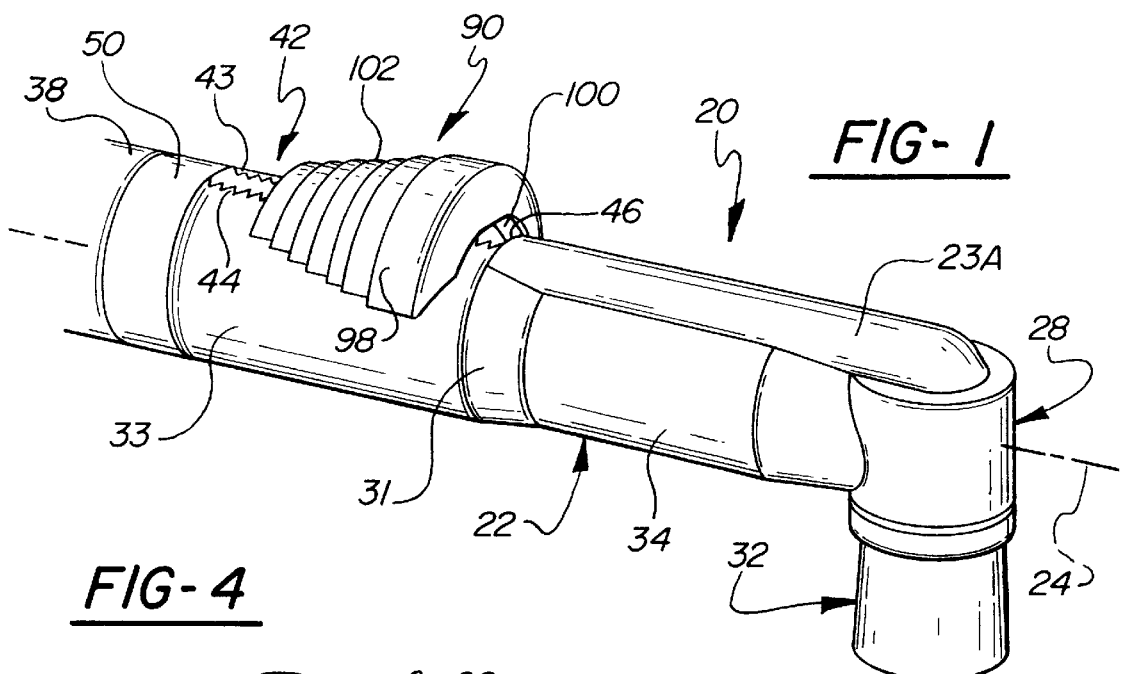
FIG-1
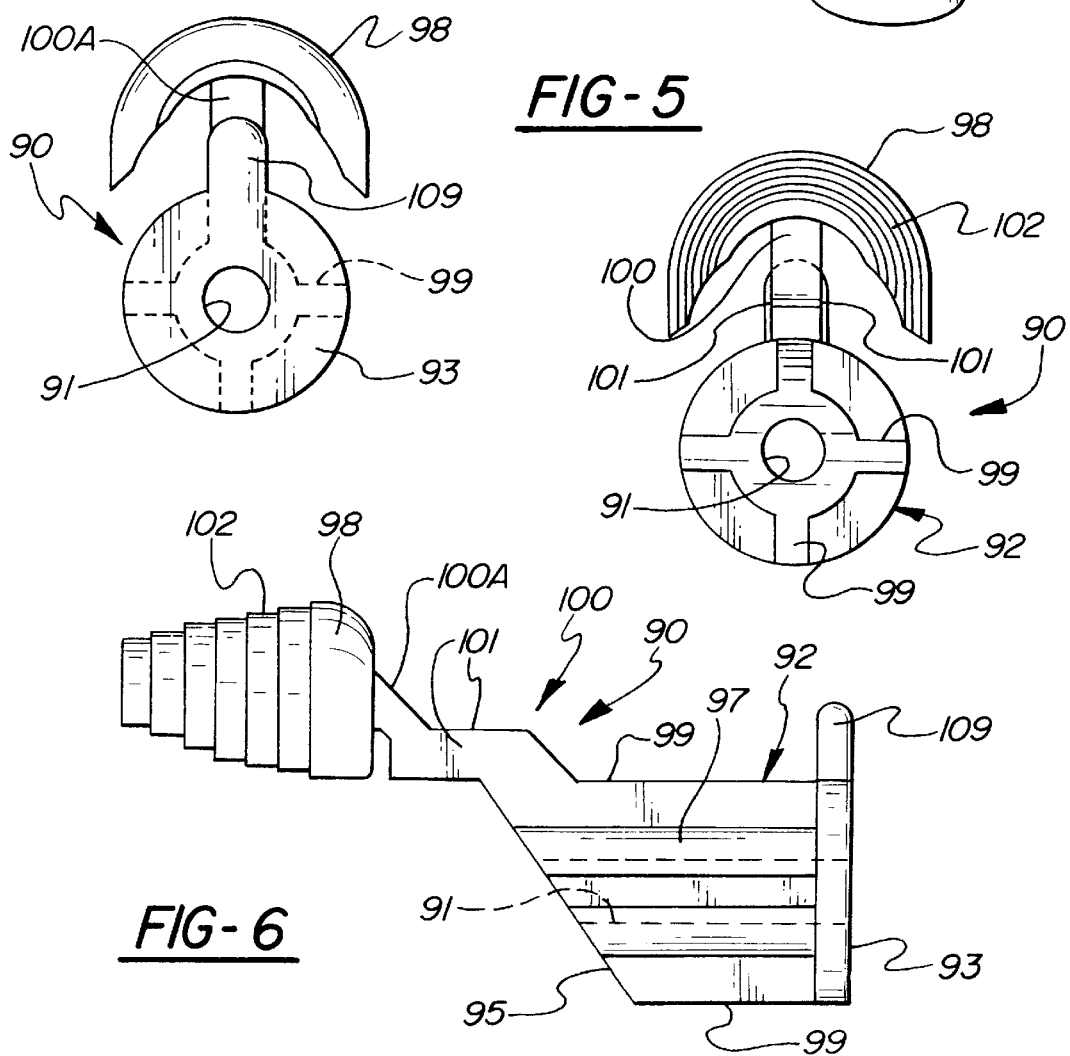
FIG-4
FIG-5
FIG-6

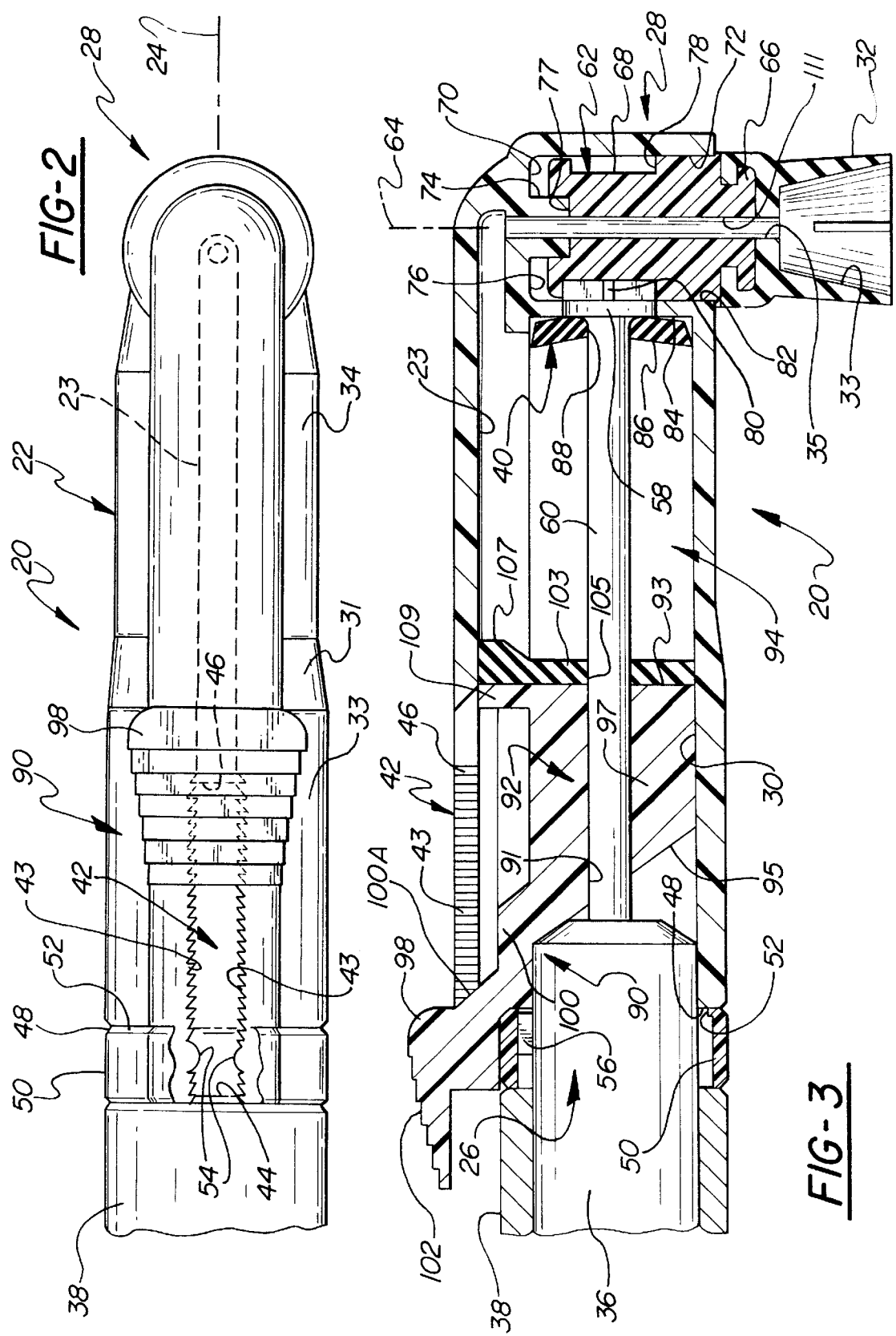

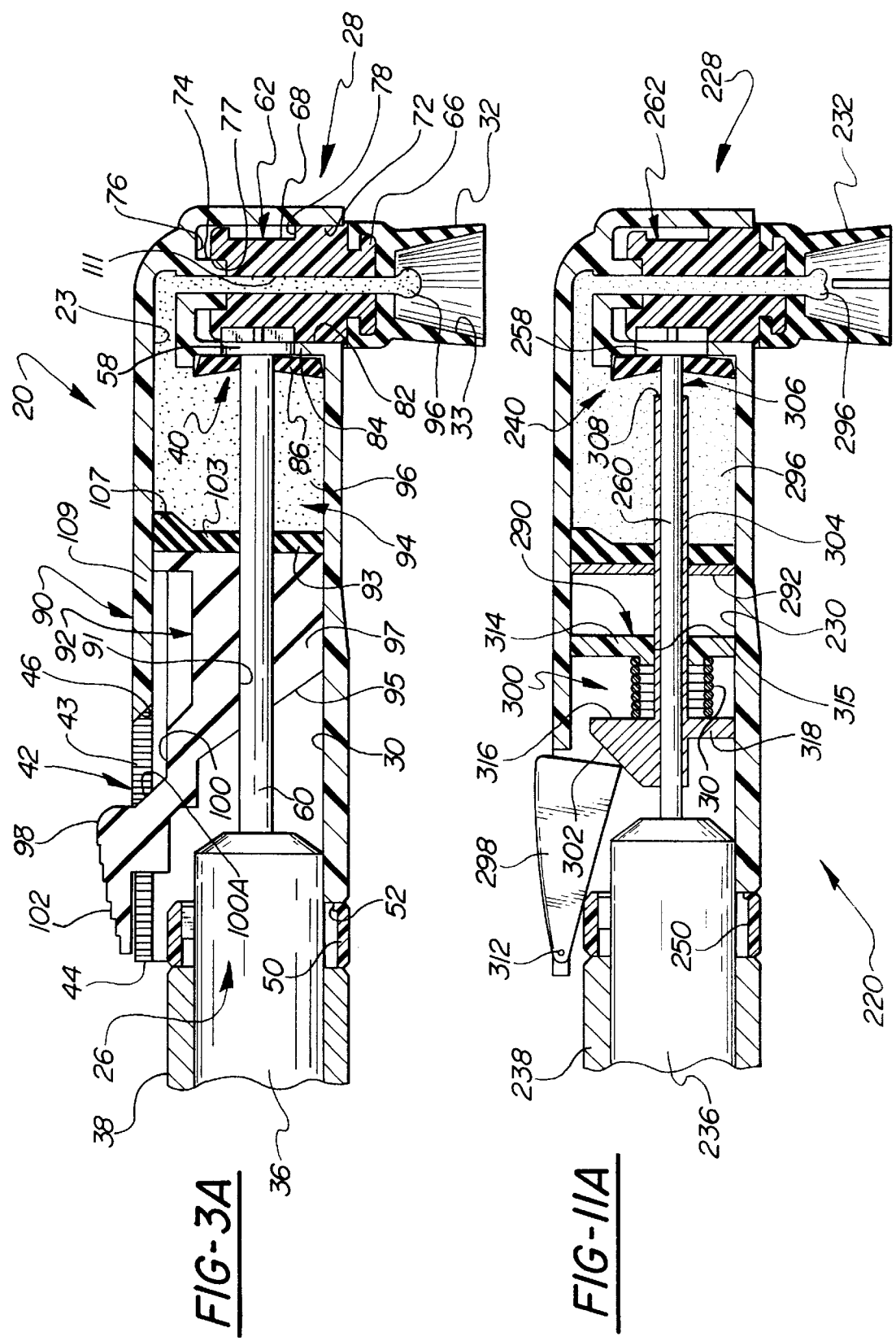

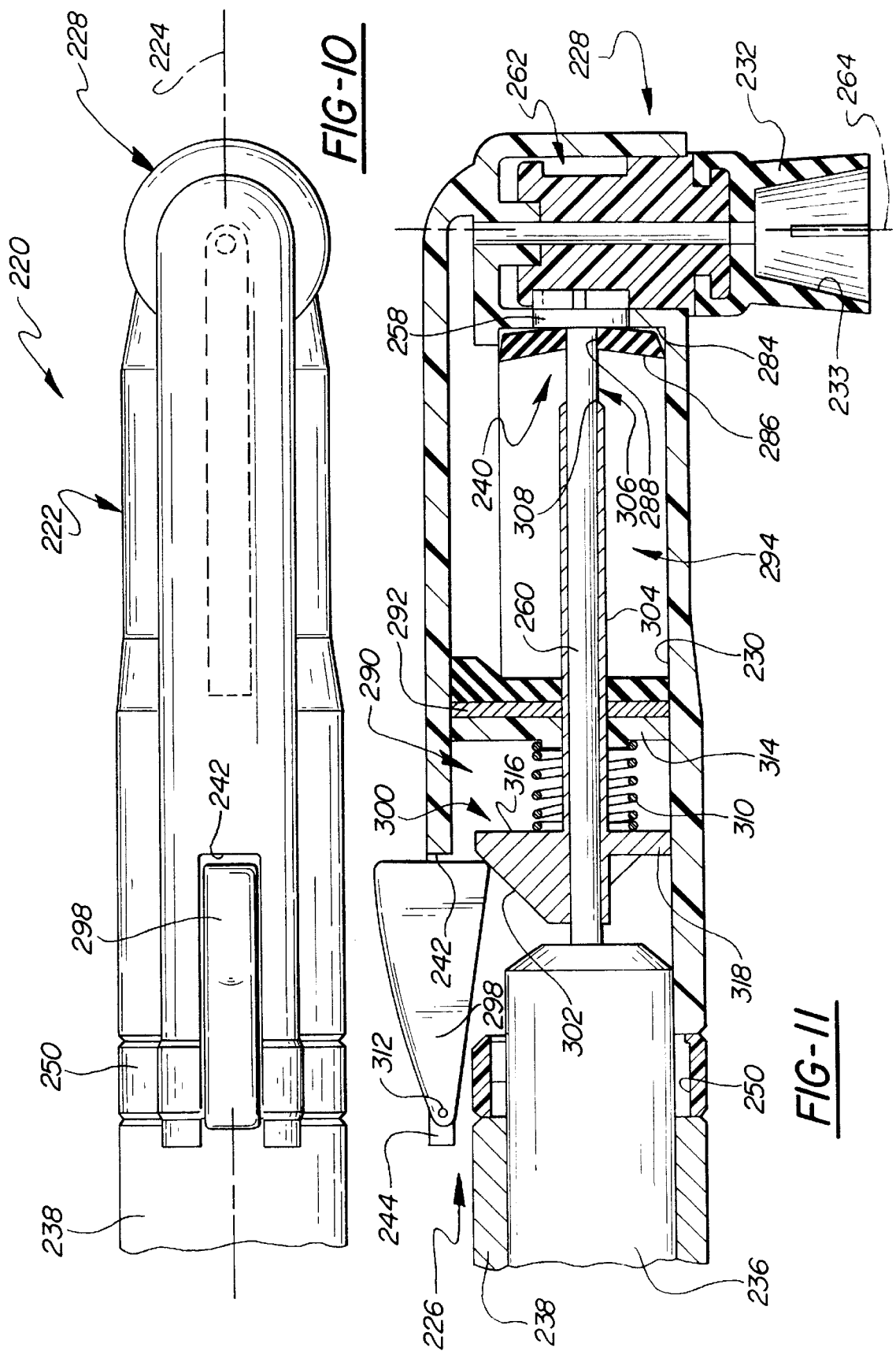

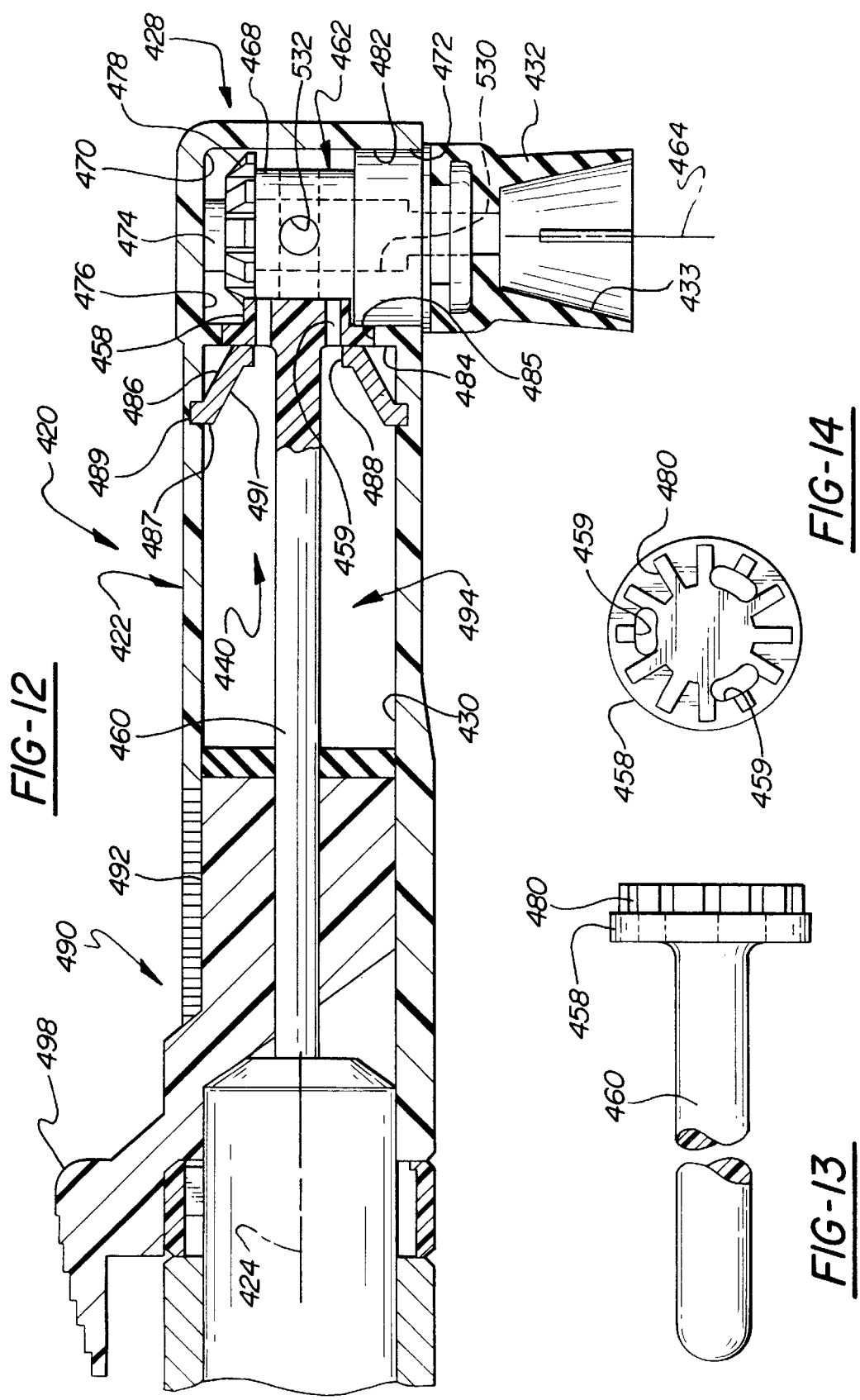

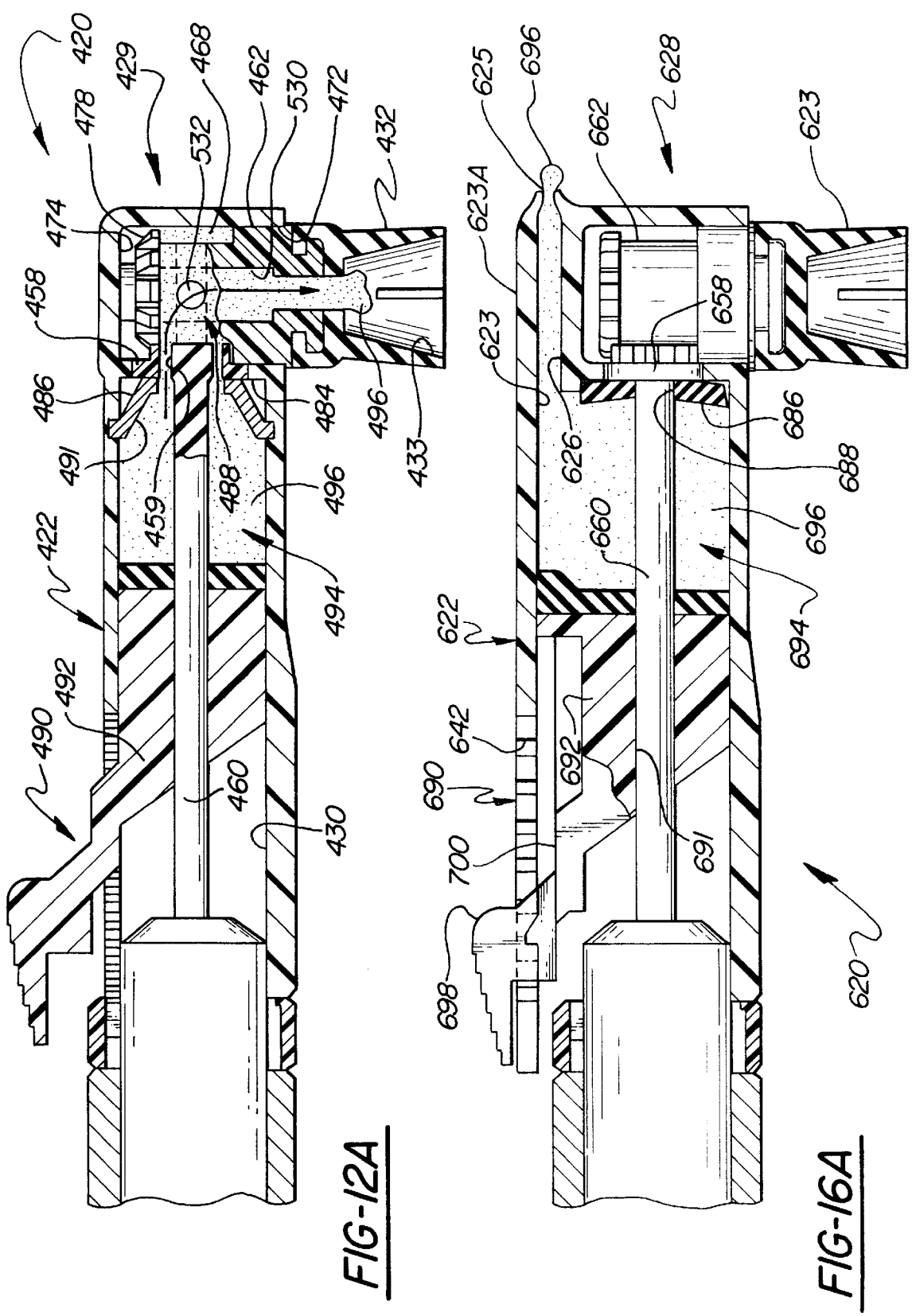

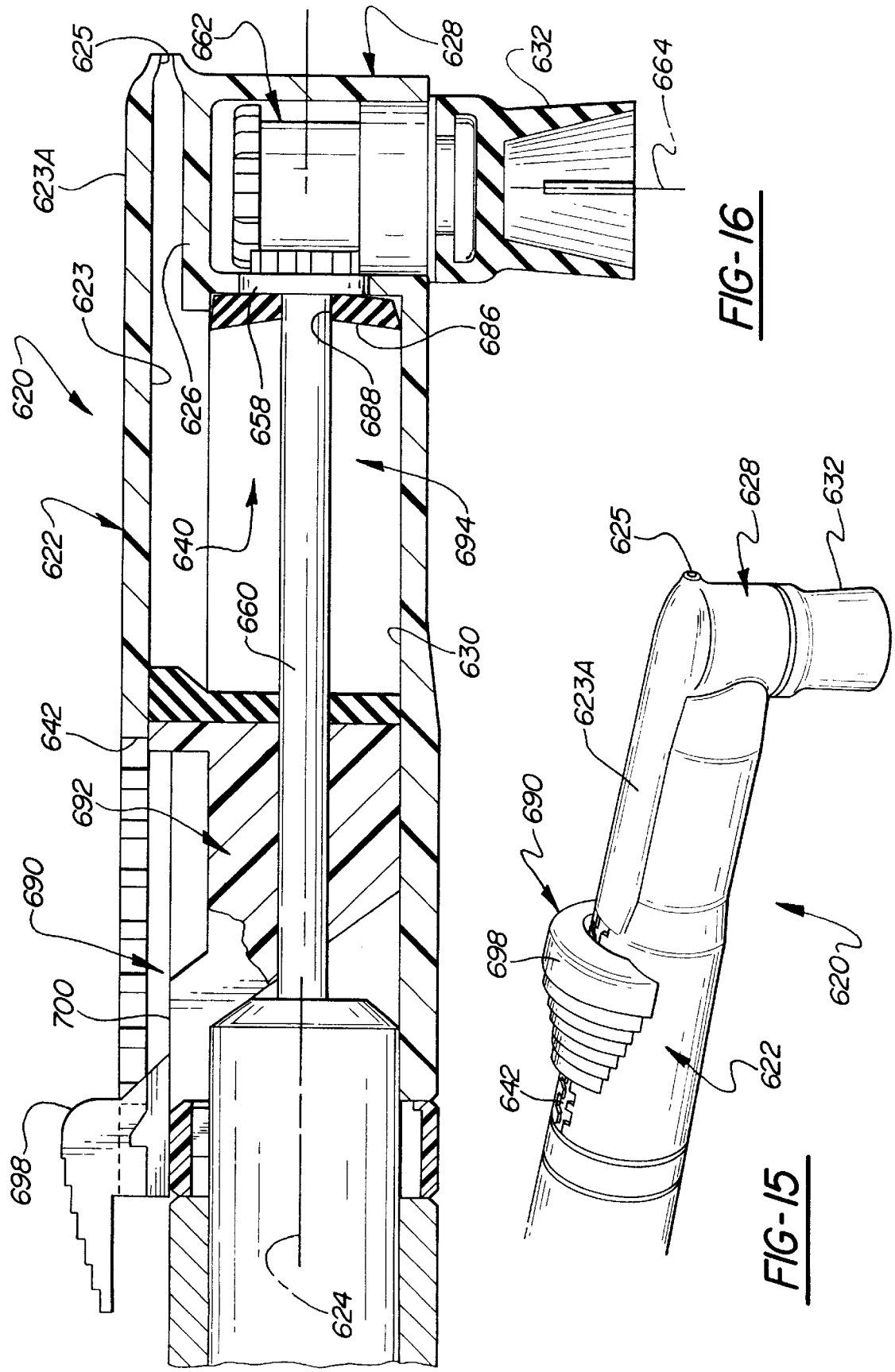

DISPOSABLE DENTAL PROPHYLAXIS ANGLE

This application claims the benefit of priority from provisional patent application Ser. No. 60/090,335, filed Jun. 23, 1998.

BACKGROUND OF THE INVENTION

1. Field of the Invention

The present invention relates, generally, to dental equipment and, more specifically, to a disposable dental prophylaxis angle for use in cleaning, polishing, bleaching, bonding, etching, or abrading teeth.

2. Description of the Related Art

Dentists, oral hygienists and their assistants employ an abrasive paste to clean and polish their patient's teeth. Similarly, other flowable dentifrice compounds are employed to bleach or abrade teeth or perform a number of other dental procedures. To this end, the dentist employs a handpiece to which is mounted a prophylaxis right angle commonly referred to in the art as a "prophylaxis angle" or "prophy angle." The prophy angle has a cup which is operatively rotated through a power source transmitted via the handpiece. The polishing paste and other flowable dentifrice may be stored in a small container. The cup is dipped into the dentifrice stored in the container and then applied to the surface of the tooth. The cup is then rotated in a lapping fashion via the powered handpiece. The rotational movement of the cup as it applies the paste cleans and polishes, bleaches or abrades the tooth. Additional amounts of dentifrice are scooped out of the container as needed and the process is repeated.

In the past, prophy angles were reusable from patient to patient. However, in modern dental practice, the prophy angle is a disposable item which is thrown away after use on one patient. Thus, modern prophy angles are usually made of plastic and are designed to be inexpensive. Similarly, the small container usually holds only enough dentifrice for one patient, and it too is disposable.

For a number of years, there has been an ongoing effort to prevent the transmission of diseases during dental procedures. Control of fluid borne diseases such as HIV, Hepatitis, and Herpes has been of particular concern to dental practitioners, not only for the sake of the patient's health, but the practitioner's as well. To combat the inadvertent transmission of such diseases, dental equipment is sterilized between each use. However, the sterilization procedure is conducted at significant cost to the dentist. The disposable dental prophylaxis right angle provided one convenient solution to the problems of transmitting fluid borne diseases between subsequent patients as well as reducing costs associated with sterilization.

Although the disposable prophy angle was a tremendous breakthrough, problems still exist relating to the application of dentifrice (paste) to the patient's teeth using the disposable prophy angle. Conventional prophy angles effectively prevent the spread of disease from patient to patient, but do not completely protect the dentist. The container of paste may be held on the finger of the practitioner. Pressure must be employed with the paste to apply it to the prophy cup of the prophy angle. This pressure often stalls the motor that drives the prophy angle. As the pressure is reduced, the motor overcomes the stall pressure, and the rotational speed of the prophy cup quickly increases, spraying buccal matter such as saliva, blood, and tissue particles. This phenomenon is commonly referred to as "splatter." Splatter can occur even in the presence of a minimal amount of buccal matter.

Attempts have been made in the past to incorporate flowable dentifrice within the prophylaxis right angle. However, these efforts have generally failed for one reason or another and prophy angles including flowable dentifrice, such as polishing paste incorporated therein have not been adopted by dental practitioners. More specifically, early prophy angles having paste incorporated therein were not disposable. Additionally, the related art suffered from the disadvantage that the paste delivery mechanisms employed in the prophy angles were relatively mechanically complex and therefore cost prohibitive. For example, disposable prophy angles having internal paste delivery systems using an auger-like structure of the type proposed in the related art must overcome problems associated with charging an internal reservoir with dentifrice material either before or after the auger is assembled into the prophy angle. Either way, the helical blades of the auger, which typically extend for a substantial portion of the internal diameter of the fluid reservoir, make it difficult to fully charge the reservoir with the dentifrice material. Also, the auger blades make advancement of the dentifrice material dependent on the direction of rotation and rotational speed of the auger. Prophy angles presently known in the related art were also too large to be practical or were generally more difficult to use and required retraining the practitioner before use on a patient.

Thus, there remains a need in the art for a disposable prophy angle which is inexpensive and effective which also promotes reducing the incidences of splatter during cleaning, polishing and other dental operations. There is also a need in the art for a disposable prophy angle which incorporates a flowable dentifrice material therein with an effective means for dispensing predetermined amounts of the material during polishing, cleaning and other dental procedures. Additionally, there remains a need in the art for such a prophy angle which is compact and not cumbersome, easy and intuitive to use and which does not require retraining before use on a patient.

SUMMARY OF THE INVENTION AND ADVANTAGES

The present invention overcomes the disadvantages in the related art in a disposable dental prophylaxis angle including an elongated housing which defines a longitudinal axis and has a central bore and a head portion in fluid communication with the central bore. A prophylaxis cup is rotatably supported by the head portion and in fluid communication with the central bore through the head portion. An actuator is movably supported by the housing and includes a piston cooperatively received and supported in the central bore. Together, the piston and central bore define a fluid chamber of decreasable volume located therebetween. A flowable dentifrice material may be contained within this chamber. The actuator is manually movable in the direction of the longitudinal axis of the housing to move the piston within the central bore in an indexing fashion, in successive increments of a predetermined distance therealong, to reduce the volume of the chamber and to force the flowable dentifrice material in predetermined, incremental amounts which correspond to the distance traveled by the piston, from the chamber to the prophy cup via the head portion.

The present invention is also embodied in a disposable dental prophylaxis angle having a slot extending for a predetermined distance along the housing. A gear train is operatively supported by the housing for imparting rotational movement to the prophylaxis cup. The gear train may include a primary, drive gear having a drive shaft extending longitudinally within the central bore of the housing and a secondary, driven gear in meshing engagement with the drive gear. The secondary, driven gear is supported within the head portion for rotation about an axis substantially perpendicular to the longitudinal axis of the housing. The prophylaxis cup is operatively mounted to the secondary, driven gear. The actuator employed in this embodiment of the present invention includes a cam which is adapted for movement through the slot. The actuator also includes a push rod having a cam follower and an isolation tube. The isolation tube is disposed about a portion of the drive shaft along a predetermined distance of the central bore, but less than the full forward extent of the drive shaft so as to present a gap between the distal end of the isolation tube and the primary drive gear. The isolation tube is adapted for rectilinear movement toward and away from the drive gear relative to the drive shaft. A piston is cooperatively received within the central bore so as to define a fluid chamber of decreasing volume disposed between the piston and the head portion. Flowable dentifrice material may be contained within this chamber. A biasing member biases the cam follower into engagement with the cam in a direction away from the drive gear. The cam is manually pivotable about a point relative to the housing and through the slot by a force acting on the pivot point to bear against the cam follower and thereby move the isolation tube in a direction toward the drive gear. The piston is operatively mounted to the isolation tube and adapted for movement therewith in one direction toward the drive gear, but is also stationary while allowing relative movement of the isolation tube in an opposite direction away from the drive gear. This results in movement of the piston within the central bore in an indexing fashion, in successive increments of predetermined distance therealong so as to reduce the volume of the chamber and thereby force the flowable dentifrice material from the chamber to the prophylaxis cup via the head portion in predetermined incremental amounts which correspond to the distance traveled by the piston along the isolation tube.

In still another embodiment of the present invention, the secondary, driven gear includes a delivery channel which extends substantially parallel to its axis of rotation and in fluid communication with the prophylaxis cup. The driven gear includes a plurality of radial, connecting ports extending transverse to, and in fluid communication with, the delivery channel in the driven gear. The drive gear includes a plurality of flow paths extending through the drive gear and in a direction substantially parallel to the longitudinal axis of the housing. The flow paths provide fluid communication between the fluid chamber and the radial, connecting ports on the driven gear. In this way, flowable dentifrice may be communicated to the prophylaxis cup. The flow paths on the drive gear are fluted such that the rotation of the drive gear in one direction promotes the flow of dentifrice material from the chamber to the radial connecting ports. The fluted flow paths are configured such that rotation of the drive gear in an opposite direction inhibits flow of the dentifrice material from the chamber to the radial connecting ports.

Still further, in another embodiment of the present invention, delivery of the dentifrice material via the secondary gear to the prophylaxis cup has been eliminated in favor of a dentifrice dispensing nipple formed in the head portion of the housing. The nipple is in fluid communication with the chamber via an upper channel portion formed in the housing. The actuator is manually movable in the direction of the longitudinal axis of the housing to move the piston within the central bore thereby reducing the volume of the chamber and forcing flowable dentifrice material from the chamber out the dentifrice dispensing nipple via this upper channel portion.

The disposable dental prophylaxis angle of the present invention has an internal dentifrice delivery system which is manually operator-controlled to dispense the dentifrice in predetermined incremental amounts which correspond to the incremental, predetermined, indexed movement of an actuator relative to the housing of the prophy angle. Thus the speed, rate, and amount of dentifrice delivered to the prophylaxis cup is independent of the rotational speed of the gear train or any other device associated with the prophy angle. The present invention therefore provides a disposable dental prophylaxis angle having an internal dentifrice delivery system which is smoothly operated with tactile feedback to the practitioner of the position of the actuator and therefore the amount of dentifrice that is delivered to the prophy cup at any given time. The present invention provides for both the delivery of dentifrice material through the head portion of the housing to the prophy cup or to a dentifrice dispensing nipple located at the distal end of the housing and above the prophy cup. Similarly, the present invention provides for dentifrice delivery through flow passages in the primary drive gear as well as the secondary driven gear of the gear train used to operatively rotate the prophy cup.

The disposable prophy angle of the present invention is relatively small and compact and approximates the size of standard prophy angles known in the art which do not include a dentifrice delivery system. Accordingly, the disposable dental prophy angle of the present invention is intuitive, easy to use and not too big or cumbersome for dental operations performed at the back of the patient's mouth.

The chamber or dental fluid reservoir of the disposable prohy angle of the present invention is also easy to charge with dentifrice material and will hold 1.0–1.25 cc of dentifrice without the need for increasing the length or circumference of the housing so as to adversely effect the dental procedures or otherwise make the use of the prophy angle counter-intuitive. In addition, the prophy angle of the present invention is cost effective to manufacture and so it meets another important need that presently exists in the related art.

Other objects, features and advantages of the present invention will be readily appreciated as the same becomes better understood after reading the subsequent description taken in connection with the accompanying drawings.

BRIEF DESCRIPTION OF THE DRAWINGS

FIG. 1 is a perspective view of one embodiment of the disposable dental prophylaxis angle of the present invention;

FIG. 2 is a top view of the disposable dental prophylaxis angle illustrated in FIG. 1 having a portion thereof broken away at the open end of the housing;

FIG. 3 is a cross-sectional side view of the dental prophylaxis angle illustrated in FIG. 2;

FIG. 3A is another cross-sectional side view of the dental prophylaxis angle shown in FIG. 3, but illustrating an advanced position of the actuator to dispense flowable dentifrice material to the prophy cup;

FIG. 4 is a front view of the actuator of the present invention;

FIG. 5 is a rear view of the actuator of the present invention;

FIG. 6 is a side view of the actuator of the present invention;

FIG. 10 is a top view of the disposable dental prophylaxis angle illustrated in FIG. 9;

FIG. 11 is a cross-sectional side view of the disposable dental prophylaxis angle illustrated in FIG. 10;

FIG. 11A is another cross-sectional side view of the disposable dental prophylaxis angle shown in FIG. 11 but illustrating the cam acting on the push rod to advance the piston along the isolation tube thereby moving flowable dentifrice material from the chamber to the prophylaxis cup;

FIG. 12 is a cross-sectional side view of another embodiment of the disposable dental prophylaxis angle of the present invention;

FIG. 12A is another cross-sectional side view of the disposable dental prophylaxis angle shown in FIG. 12 but illustrating the actuator advanced within the housing to move the flowable dentifrice material through the flow paths in the drive and driven gears to the prophylaxis cup;

FIG. 13 is a side view of the primary drive gear and drive shaft employed in the embodiments of FIGS. 12 and 12A of the present invention;

FIG. 14 is an end view of the primary drive gear employed in the embodiments in FIG. 12 of the present invention;

FIG. 15 is a perspective view of another embodiment of the disposable dental prophylaxis angle of the present invention;

FIG. 16 is a cross-sectional side view of the disposable dental prophylaxis angle illustrated in FIG. 15; and FIG. 16A is another cross-sectional side view of the disposable dental prophylaxis shown in FIG. 16 but illustrating the actuator advanced within the housing to move dentifrice material from the chamber through the dentifrice dispensing nipple formed in the head portion of the housing.

DETAILED DESCRIPTION OF THE PREFERRED EMBODIMENT(S)

Figure 7:
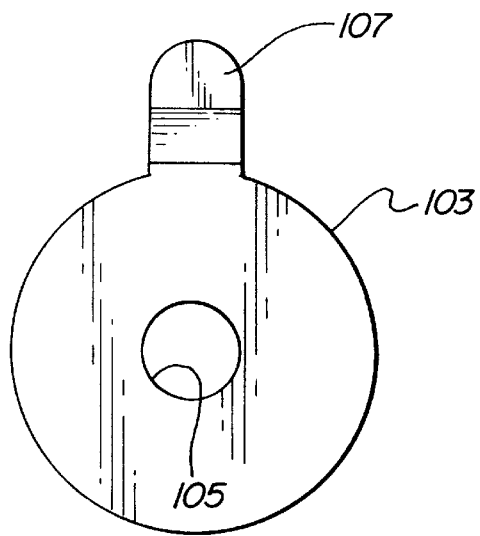
FIG. 7 is an end view of the plunger seal of the present invention.

The present invention overcomes the deficiencies in the related art in a disposable prophylaxis right angle or "prophy angle" having an internal, flowable dentifrice delivery system. The present invention may be employed by dentists, oral hygienists and/or dental assistants for cleaning, polishing, bleaching, bonding, etching or abrading a patient's teeth. Thus, and as will be made clear from the description which follows, the flowable dentifrice may include a variety of fluid agents including, for example, abrasive pastes, polishing compounds, lubricants, bleaching agents, bonding agents and etchings. Furthermore, those having ordinary skill in the art will appreciate that the present invention is in no way limited to the composition of, or specific use for, the flowable dentifrice material employed with the prophy angle of the present invention.

Referring now to the drawings, one embodiment of the present invention is generally shown at 20 in FIGS. 1–3A. The disposable dental prophylaxis angle 20 includes an elongated shell-like housing, generally indicated at 22, defining a longitudinal axis 24. The housing 22 has an open end 26, a head portion, generally indicated at 28, disposed opposite the open end 26 and a central bore 30 extending therebetween. A flexible prophylaxis cup or "prophy cup" 32 is rotatably supported by the head portion 28 and is in fluid communication with the central bore 30 as will be discussed in greater detail below. The prophy cup 32 may vary in size, texture and flexibility as dictated by the procedure or preference of the practitioner.

The housing 22 is substantially cylindrical in shape in the direction of the longitudinal axis 24 and may taper, for example, at 31 from a larger diameter 33 near the open end 26 of the housing 22 to a smaller diameter 34 near the head portion 28. The housing 22 may be manufactured from plastic or any other suitable, inexpensive material using an injection molded process or otherwise to form an inexpensive prophylaxis angle 20 which may be discarded after use on a single patient.

The open end 26 of the housing 22 is adapted to receive the nose cone 36 of a dental handpiece 38. The handpiece 38 operatively powers the prophylaxis cup 32 for rotation relative to the head portion 28 via a gear train, generally indicated at 40, as will be discussed in greater detail below.

The housing 22 also includes a slot, generally indicated at 42, having an open end 44. The slot 42 extends from the open end 26 of the housing for a predetermined distance therealong. The slot 42 terminates in a closed, distal end 46. In the preferred embodiment, the slot 42 extends in a direction parallel to, but spaced from, the longitudinal axis 24 of the housing 22.

As best shown in FIG. 2, an annular groove 48 is disposed about the circumference of the housing 22 adjacent the open end 26 thereof. An annular collar 50 is also disposed about the circumference of the housing 22 but is adapted for sliding movement in an axial direction relative to the housing 22. When the annular collar 50 is moved to its rearwardmost position as illustrated in FIGS. 2 and 3, a lip 52 formed thereon is receivable in the annular groove 48. In this disposition, the collar 50 extends in overlapping relationship between the housing 22 and the handpiece 38 and acts to stabilize the prophy angle 20 relative to the handpiece 38. A portion of FIG. 2 is broken away at this juncture to illustrate that the slot 42 includes a pair of opposed tabs 54 spanning a portion of the slot 42 and extending toward one another adjacent the open end 44 of the slot 42. As best shown in FIG. 3, the slot 42 is adapted to receive and retain an anti-rotation nipple 56 which projects from the handpiece 38. The opposed tabs 54 come into frictional engagement with the anti-rotation nipple 56. Thus, the tabs 54 assist in fixing the prophy angle 20 to the handpiece 38 against movement in a direction parallel to the longitudinal axis 24 of the housing 22. Likewise, the anti-rotation nipple 56 prevents the prophy angle 20 from spinning relative to the handpiece 38 due to torque imparted to the gear train 40. Similarly, the collar 50 resists cantilever forces acting on the prophy angle 20 relative to the handpiece 38 and further acts to stabilize the prophy angle 20 relative to the handpiece 38.

As noted above, the gear train 40 is operatively supported by the housing 22 and imparts rotational movement to the prophylaxis cup 32. Referring now specifically to FIG. 3, the gear train 40 includes a primary drive gear 58 having a drive shaft 60 extending longitudinally within the central bore 30 and a secondary, driven gear, generally indicated at 62, in meshing engagement with the drive gear 58. The secondary, driven gear 62 is supported within the head portion 28 for rotation about an axis 64 which extends substantially perpendicular to the longitudinal axis 24 of the housing 22. The prophylaxis cup 32 is operatively mounted to the secondary driven gear 62 via interaction in a conventional manner with a flanged extension 66 depending from the driven gear 62.

More specifically, the secondary, driven gear 62 includes a body 68 which is supported in a cavity 70 defined by the head portion 28. The cavity 70 is open-ended at 72 in the axial direction and includes an annular bearing 74 depending from the upper wall 76 of the head portion 28. The bearing 74 is received in an annular socket 77 formed at the top of the driven gear body 68. Gear teeth are formed at 78 on the driven gear body 68 to mesh with corresponding teeth 80 on the primary drive gear 58. The body 68 may also include an annular bearing 82 to further stabilize the secondary driven gear 62 as it rotates relative to the head portion 28.

The housing 22 further defines an end wall 84 at the distal end of the central bore 30 opposite the open end 26 of the housing 22. The gear train 40 includes an annular retaining clip 86 which is adapted for an interference fit within the central bore 30 at the end wall 84 and adjacent the head portion 28. The retaining clip 86 serves to lock the drive gear 58 into meshing engagement with the driven gear 62. In addition, the retaining clip 86 includes an aperture 88. The drive shaft 60 is supported for rotation by the retaining clip 86 through the aperture 88 adjacent the head portion 28. In addition, the retaining clip 86 serves as a barrier against flow of dentifrice material into the meshing gears 58, 62 of the gear train.

The primary and secondary gears 58, 62 are preferably manufactured from plastic and employ a 2:1 gear ratio. This step-down gear ratio assists the practitioner in effecting better control of the rotational speed of the prophylaxis cup 32 during dental procedures and thereby helps to resist incidents of splatter. This increases the range of the effective air pressure used to power the motor in the handpiece 38 by twofold. Concomitantly, the 2:1 gear ratio decreases the chance that the prophy cup will spin too fast thereby heating the tooth or burning, or cutting gingival (gum) tissue.

The prophylaxis angle 20 of the present invention also includes an actuator, generally indicated at 90. The actuator 90 is movably supported by the housing 22 in the general direction of the slot 42. The actuator 90 includes a piston 92 which is cooperateively received and supported in the central bore 30 of the housing to define a fluid chamber, generally indicated at 94. The chamber 94 is located between the piston 92 and the head portion 28 and houses a flowable dentifrice material 96 (FIG. 3A). The chamber 92 is of decreasable volume as will be described in greater detail below.

The actuator 90 is manually movable in the direction of the longitudinal axis 24 of the housing 22 to move the piston 92 within the central bore 30 in an indexing fashion. Importantly, the actuator 90 moves in successive increments of a predetermined distance along the longitudinal axis 24 of the housing 22 to reduce the volume of the chamber 94 concomitantly and thereby force the flowable dentifrice material 96 in predetermined incremental amounts which correspond to the distance traveled by the piston 92 from the chamber 94 to the prophylaxis cup 32 via the head portion 28. More specifically, and in the preferred embodiment illustrated in FIGS. 4–6, the actuator 90 is an integrally molded part including a knob 98 supported adjacent to the housing 22 and exterior of the central bore 30 and a neck portion 100 interconnecting the knob 98 an the piston 92. As such, the neck portion 100 extends through the slot 42. As best shown in FIGS. 1, 4 and 5, the knob 98 has an arcuate profile and extends about the cylindrical housing 22 for a predetermined arcuate extent thereof. The knob 98 has a textured surface 102 which is adapted for manual manipulation by fingers and thumbs as will be described in greater detail below.

The knob 98 is movable relative to the slot 42 in a direction parallel to, but spaced from, the longitudinal axis 24 defined by the housing 22. The neck portion 100 cooperates with the slot 42 to produce the successive, incremental, indexed movement of the piston 92 in the central bore 30 under the influence of a force acting on the knob 98. More specifically, the slot 42 includes a pair of opposed, serrated surfaces 43 (FIGS. 2 and 3) which extend from the tabs 54 for a major extent of the slot 42 toward the closed, distal end 46 thereof. The neck portion 100 includes a pair of complementary surfaces 101 which cooperate with the serrated surfaces 43 on the slot 42 to provide successive, incremental, indexed movement of the neck portion 100 (and therefore the actuator 90) relative to the slot 42. The neck portion 100 includes a stop surface 100A disposed for abutting contact with the distal end 46 of the slot 42. Thus, the stop surface 100A serves to limit the longitudinal distance traveled by the piston 92 in the central bore.

The piston 92 is defined by a plunger 93, a force stabilizing surface 95, and a ram portion 97 extending therebetween. The force stabilizing surface 95 extends from the neck portion 100 in a direction so as to define an obtuse angle with the ram portion 97 of the piston 92 and so as to mitigate any moment forces acting through the piston 92 due to forces acting on the knob 98 to move it at a distance radially spaced from the longitudinal axis 24 of the housing 22.

As best shown in FIG. 5, the ram portion 97 includes a plurality of ribs 99 extending radially outward therefrom between the force stabilizing surface 95 and the plunger 93. The piston 92 includes an axial passage 91 which extends therethrough in a direction substantially parallel to the central bore 30. The axial passage 91 is adapted to receive and support the drive shaft 60 of the gear train 40. Obviously then, the piston 92 moves axially relative to the rotating drive shaft 60 of the gear train 40 as the volume of the chamber 94 is decreased. While as shown in the preferred embodiment, the actuator 90 is a integrally molded, one-piece, plastic part it will be appreciated that the actuator 90 may be manufactured in more than one piece.

Figure 8:
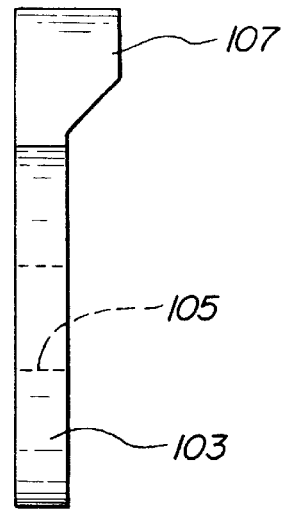
FIG. 8 is a side view of the plunger seal illustrated in FIG. 7.

A plunger seal 103 is mounted to the plunger 93 and cooperates with the central bore 30 to form a seal between the piston 92 and the central bore 30 at one end of the chamber 94. As best shown in FIGS. 7 and 8, the plunger seal 103 is substantially annular in shape and thereby complements not only the shape of the plunger 93 but the central bore 30 as well. Like the piston 92, the plunger seal 103 has an aperture 105 through which the drive shaft 60 passes. Quickly referring now to FIGS. 1 and 3, it can be seen that the housing 22 includes an upper channel portion 23 (identified by the ridge 23 formed on the outer surface of the housing 22 as illustrated in FIG. 1). The upper channel portion 23 is defined in the chamber 94 and is radially spaced from the longitudinal axis 24 of the housing 22. The plunger seal 103 includes a tabbed portion 107 which is received in the channel portion 23 to seal same relative to the central bore 30 at the piston 92. Correspondingly, the plunger 93 includes a backing portion 109 disposed adjacent to the tab portion 107 of the plunger 103 for supporting same as the piston 92 is moved within the central bore 30 to reduce the volume of the chamber.

The upper channel portion 23 provides fluid communication between the chamber 94 and the interior surface 33 of the prophylaxis cup 32 via a delivery channel 111 extending substantially parallel to the axis of rotation 64 of the secondary driven gear 62.

In its operative mode, the prophylaxis angle 20 of the present invention is mounted to a handpiece 38 which imparts rotational movement to the primary drive gear 58 in a manner conventionally known in the art. The primary drive gear 58, in turn, drives the secondary driven gear 62. The secondary, driven gear 62 rotates about an axis 64. The prophylaxis cup 32 used to perform various dental procedures on a patient's teeth is connected to, and rotates with, the secondary driven gear 62. During such a procedure, the dental practitioner may wish to deliver dentifrice material 96 (FIG. 3A), such as polishing paste, to the prophylaxis cup 32. This is accomplished by advancing the actuator 90 relative to the housing 22. More specifically, a force is applied to the knob 98 to advance the piston 92 within the central bore 30. As the piston 92 is advanced, the volume of the chamber 94 decreases. In this way, the flowable dentifrice material is advanced within the housing 22 from the chamber 94 to the interior surface 33 of the prophylaxis cup 32 as the actuator 90 is advanced incrementally relative to the housing 22. The dentifrice material 96 flows in a controlled fashion in response to manual, operator input from the chamber 94 through the upper channel 23 into the delivery channel 111 of the secondary driven gear 62 and then to the prophylaxis cup 32 via a port 35 formed therein. Thus, the dentifrice material 96 is delivered to the prophylaxis cup 32 independent of the rotational speed of the gear train 40.

At any given position of the actuator 90 relative to the housing 22, the force on the knob 98 may be relieved. The actuator 90 will then be fixed in its relative position against any rearward movement toward the open end 44 of the slot 42. The actuator 90 may be moved again in a direction toward the head portion 28 pursuant to operator input until the stop surface 100A on the neck portion 100 abuts the distal end 46 of the slot 42.

Another embodiment of the present invention is generally indicated at 220 in FIGS. 9–11A where like numerals, increased by a factor of 200, are used to designate like structure with respect to the prophylaxis angle 20 illustrated in FIGS. 1–3A. The description of the embodiment illustrated in FIGS. 9–11A will focus primarily upon the structure and features which differ from that shown in FIGS. 1–3A. Accordingly, and unless otherwise specified, it should be inferred that, where like structure is incorporated into the embodiment of FIGS. 9–11A, this structure operates in a substantially similar manner as that illustrated in FIGS. 1–3A.

Figure 9:
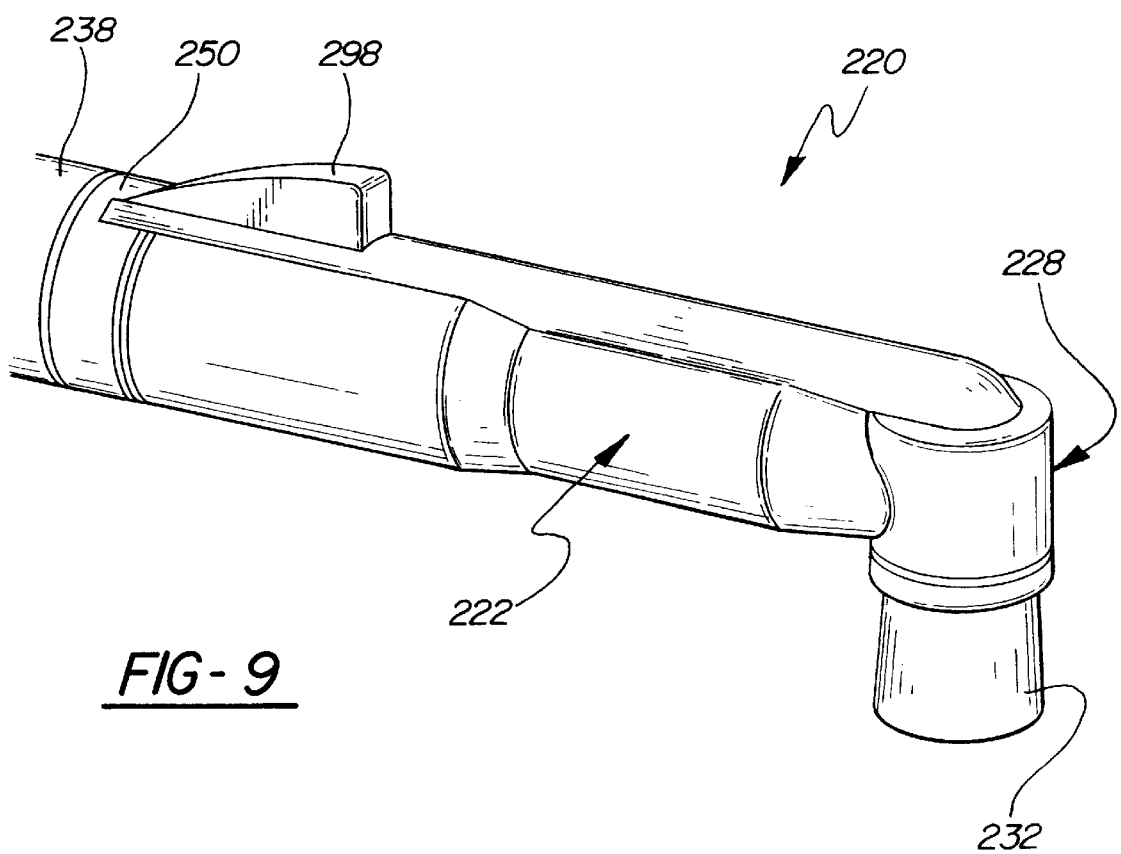
FIG. 9 is a perspective view of another embodiment of the disposable dental prophylaxis angle of the present invention.

Referring now to the FIGS. 9–11, the disposable dental prophylaxis angle 220 includes an elongated shell-like housing, generally indicated at 222, defining a longitudinal axis 224. The housing 222 has an open end 226, a head portion 228 disposed the opposite end 226 with a central bore 230 extending therebetween. The head portion 228 is in fluid communication with the central bore 230 as will be discussed in greater detail below.

The housing 222 is substantially cylindrical in shape in the direction of the longitudinal axis 220 and may taper like the housing 22 illustrated in FIGS. 1–3A. Similarly, the housing 222 may be manufactured from plastic and is designed to be discarded after use on a single patient. The open end 226 of the housing 222 is adapted to receive the nose cone 236 of a dental handpiece 338. The handpiece 238 operatively powers the prophylaxis cup 232 for rotation relative to the head portion 228 via a gear train, generally indicated at 240, as will be described in greater detail below.

The housing 222 also includes a slot 242 which may have an open end 244 extending from the open end 226 of the housing for a predetermined distance. In the preferred embodiment, the slot 242 extends in a direction parallel to, but spaced from, the longitudinal axis 242 of the housing 20.

The open end 226 of the housing 222 is adapted to receive the nose cone 236 of a handpiece 238. An annular collar 250 is adapted for sliding movement in the axial direction of the housing 222 so as to extend in overlapping relationship with the housing 222 and the handpiece 238 in a manner described with respect to FIGS. 1–3A.

As noted above, the gear train 240 is operatively supported by the housing 222 for imparting rotational movement to the prophylaxis cup 232. To this end, the gear train 240 includes a primary drive gear 258 having a drive shaft 260 extending longitudinally within the central bore 230 and a secondary, driven gear, generally indicated at 262, in meshing engagement with the drive gear 258. The secondary, driven gear 262 is supported within the head portion 228 for rotation about an axis 264 which is substantially perpendicular to the longitudinal axis 224 of the housing 222. The prophylaxis cup 232 is operatively mounted to the secondary driven gear 262 in a conventional manner as described above.

The housing 222 further defines an end wall 284 at the distal end of the central bore 230 opposite the open end 226 of the housing 222. The gear train 240 includes an annular retaining clip 286 which is adapted for an interference fit within the central bore 230 at the end wall 284 and adjacent to the head portion 228 for locking the drive gear 258 into meshing engagement with the driven gear 262. The retaining clip 282 includes an aperture 288. The drive shaft 260 is supported for rotation by the retaining clip 282 through the aperture 288 adjacent to the head portion 228. The primary and secondary gears 258, 262, respectively, are preferably manufactured from plastic and employ a 2:1 gear ratio.

The disposable prophylaxis angle 220 of the present invention further includes an actuator 290 which is movably supported by the housing 222. The actuator 290 includes a cam 298 which is adapted for movement through the slot 242. Further, the actuator 290 includes a push rod 300 having a cam follower 302 and an isolation tube 304. The isolation tube 304 is disposed about a portion of the drive shaft 260 along a predetermined distance of the central bore 230, but less than the full, forward extent of the drive shaft 260 so as to provide a gap 306 between the distal end 308 of the isolation tube 304 and the primary drive gear 358. The isolation tube 304 is adapted for rectilinear movement toward and away from the drive gear 258 relative to the drive shaft 260 as will be discussed in greater detail below.

A piston 292 is cooperatively received within the central bore 230 to define a fluid chamber 294 of decreasable volume disposed between the piston 292 and the head portion 228. Flowable dentifrice material 296 is contained within the chamber 294 (FIG. 11A).

A biasing member 310 biases the cam follower 302 into engagement with the cam 298 in a direction away from the drive gear 258. The cam 298 is manually pivotable about a point 312 relative to the housing 220 and through the slot 242 by a force acting about the pivot point 312. In this way, the cam 298 bears against the cam follower 302 to move the isolation tube 304 in a direction toward the drive gear 258.

The piston 292 is operatively mounted to the isolation tube 304 and is adapted for movement therewith in one direction toward the drive gear 258. However, the piston 292 is stationary within the central bore 230 while allowing relative movement of the isolation tube 304 in an opposite direction away from the drive gear. As best shown in FIG. 11A, this arrangement cooperates to result in movement of the piston 292 within the central bore 230 in an indexing fashion, in successive increments of predetermined distance therealong to reduce the volume of the chamber 294 and thereby force flowable dentifrice material 296 from the chamber 294 to the prophylaxis cup 232 via the head portion 228 in predetermined incremental amounts corresponding to the distance traveled by the piston 292 along the isolation tube 304. The predetermined incremental distance that the piston 292 moves within the central bore 230 to reduce the volume of the chamber 294 is limited to the extent of the gap 306 between the distal end 308 of the isolation tube 304 and the primary drive gear 358.

A dam 314 is cooperatively received within the central bore 230 and is axially fixed relative to the housing 222. The push rod 300 includes a spring retainer 316. The biasing member includes a coiled spring 310 disposed about a portion of the isolation tube 304 and between the fixed dam 314 and the spring retainer 316 to bias the push rod 300 away from the drive gear 258. In the preferred embodiment, the spring retainer 316 is formed integrally with the cam follower 302 and has a lower depending leg 318 adapted for sliding contact with the central bore 230 and for supporting the push rod 300 as it is moved rectilinearly within the central bore 230. In addition, and as illustrated in the Figures, the push rod 300 may be an integral, one-piece molded part.

The dam 314 includes an axial passage 315 which extends therethrough in a direction substantially parallel to the central bore 230. The axial passage 315 is adapted to receive and support the isolation tube 304 for rectilinear movement toward and away from the drive gear 258.

The disposable prophy angle 220 operates in a manner substantially similar to the prophy angle 20 illustrated in FIGS. 1–3A. The cam 298 bears upon the cam follower 302 of the push rod 300 to incrementally advance the isolation tube 305 in the direction of the primary gear drive 358 across a substantial portion of the gap 306 between the distal end 308 of the isolation tube 304 and the drive gear 358. Rectilinear movement of the isolation tube 304 causes the piston 292 to be advanced therealong in indexing fashion, in successive increments of predetermined distance to reduce the volume of the chamber 294 and thereby force flowable dentifrice material 296 from the chamber 294 to the prophylaxis cup 232 via the head portion 282 in predetermined incremental amounts. These amounts will correspond to the distance traveled by the piston 292 along the isolation tube 304. Thus, the dentifrice material 296 flows in a controlled fashion in response to manual, operator input from the chamber 294 through the upper channel 223 into the delivery channel of the secondary, driven gear 62. Accordingly, and like the previous embodiment discussed above, the dentifrice material 296 is delivered to the prophylaxis cup 32 independent of the rotational speed of the gear train 40.

Furthermore, and after any given incremental advancement of the piston 292 along the isolation tube 304, the piston is fixed in its forward relative position against any rearward movement while, at the same time, allowing relative rearward movement of the isolation tube 304.

Another embodiment of the present invention is generally indicated at 420 in FIGS. 12, 12A and 13–14 where like numerals, increased by a factor of 400 with respect to the disposable prophylaxis angle 20 illustrated in FIGS. 1–3A, are used to designate like structure. There, the disposable prophylaxis angle 420 includes an elongated housing 422 which defines a longitudinal axis 424 having a central bore 430 and a head portion 428 in fluid communication with the central bore 430 as will be explained in greater detail below. A prophylaxis cup 432 is rotatably supported by the head portion 428 and is in fluid communication with the central bore 430 through the head portion 428.

The disposable dental prophylaxis angle 420 further includes an actuator 490 of the type described in FIGS. 1–6. Accordingly, the actuator 490 is supported by the housing 422 and includes a piston 492 which is cooperatively supported within the central bore 430 to define a fluid chamber 494 (FIG. 12A). The chamber 494 has a decreasable volume which is disposed between the piston 492 and the head portion 428. Flowable dentifrice material 496 is contained within the chamber 494. The actuator 490 is manually movable to move the piston 492 within the central bore 430 so as to reduce the volume of the chamber 494 to force the flowable dentifrice material 496 from the chamber 494 to the prophy cup 432 via the head portion 428. The flow path of the dentifrice material 496 differs from that disclosed in the earlier embodiments discussed above in that the housing 422 does not include an upper channel portion and the dentifrice material flows through the end wall 484 of the central bore 430 and through the primary and secondary gears 458, 462, respectively, as will be described in greater detail below.

Like the embodiments described above, a gear train 440 is operatively supported by the housing 422 to impart rotational movement to the prophylaxis cup 432. The gear train 440 includes a primary drive gear 458 having a drive shaft 460 extending longitudinally within the central bore 430. In addition, the gear train 440 includes a secondary, driven gear 462 in meshing engagement with the drive gear 458 and supported within the head portion 428 for rotation about an axis 464 which is substantially perpendicular to the longitudinal axis 424 of the housing 422. The prophylaxis cup 432 is conventionally mounted to the secondary, driven gear 462.

The secondary, driven gear 462 includes a body 468 which is supported in a cavity 470 defined by the head portion 428. The cavity 470 is open-ended at 472 in the axial direction and includes an annular bearing 474 depending from the upper wall 476 of the head portion 428. The bearing 474 is received in an annular socket formed at the top of the driven gear body 468. Gear teeth are formed at 478 on the body 468 to mesh with corresponding teeth 480 (best shown in FIG. 13) on the primary drive gear 458. The body 468 may also include an annular bearing 482 to further stabilize the secondary, driven gear 462 as it rotates relative to the head portion 428.

In addition, the secondary, driven gear 462 includes a stepped delivery channel 530 extending substantially parallel to the axis of rotation 464 thereof and in fluid communication with the interior surface 433 of the prophylaxis cup 432. A plurality of radial, connecting ports 532 extend transverse to, and in fluid communication with, the delivery channel 530 in the driven gear 462. Like the embodiments disclosed above, the gear train 440 includes a 2:1 gear ratio between the drive gear 458 and the driven gear 468. In addition, the gear train 440 includes a retaining clip 486 having an annular tang 487 which is adapted for interference fit within an annular groove 489 formed in the central bore 430 adjacent the head portion 428. The retaining clip 486 serves to lock the drive gear 458 into meshing engagement with the driven gear 462.

The retaining clip 486 includes an aperture 488 which corresponds to a hole 485 in the end wall 484 of the central bore 430. The drive shaft 460 is supported for rotation adjacent the head portion 428 by the retaining clip 486 through the aperture 488. The retaining clip 488 also defines a frustoconically-shaped interior surface 491 which narrows the chamber 494 adjacent to the drive gear 462. In this way, the frustoconical-shaped interior surface 491 directs flowable dentifrice material 496 from the chamber 494 toward the drive gear 458 for a purpose which will be explained below.

As best shown in FIGS. 12, 12A and 14, the drive gear 458 includes a plurality of flow paths 459 extending through the drive gear 458 in a direction substantially parallel to the longitudinal axis 424 of the housing 422. These flow paths 459 provide fluid communication between the chamber 494 and the radial connecting ports 532 on the driven gear 462. Accordingly and as shown in FIG. 12A, the flowable dentifrice 496 is communicated to the prophylaxis cup 432 in this embodiment through the flow paths 459 in the drive gear 458 through the radial connecting ports 532 and the delivery channel 530 to the interior surface 433 of the prophylaxis cup 432.

Furthermore, the flow paths 459 are fluted such that rotation of the drive gear 458 in one direction promotes the flow of the dentifrice material 486 from the chamber 494 to the radial connecting ports 532. In addition, and due to the fluted shape of the flow paths 459, rotation of the drive gear 458 in an opposite direction inhibits the flow of the dentifrice material 496 from the chamber 494 to the radial connecting ports 532. Ultimately, however, the flow of the dentifrice material 496 to the prophylaxis cup 432 is primarily influenced by the operator-controlled movement of the actuator 490 relative to the housing 422. But the fluted flow paths 459 provide the operator with an even greater level of control over the dispensing of the dentifrice material 496 into the prophylaxis cup 432 and, therefore, the application of this material to the patient's teeth.

Another embodiment of the present invention is generally indicated at 620 in FIGS. 15, 16 and 16A, where like numerals, increased by a factor of 600 with respect to the disposable prophylaxis angle 20 illustrated in FIGS. 1–3A, are used to designate like structure.

The disposable dental prophylaxis angle 620 illustrated in FIGS. 15–16A includes an elongated housing 622 defining a longitudinal axis 624 and having a central bore 630 as well as a head portion 628. A prophylaxis cup 632 is rotatably supported in the head portion 628. The disposable prophylaxis angle 620 also includes an actuator 690 of the type described above with respect to FIGS. 1–6. Thus, the actuator 690 is movably supported by the housing 622 and includes a piston 692 which is cooperatively received and supported within the central bore 630 so as to define a fluid chamber 694. The chamber 694 has a decreasable volume which is disposed between the piston 692 and the head portion 628. Flowable dentifrice material 696 may be contained within the chamber 694 (FIG. 16A).

The housing 622 is substantially cylindrical in the direction of the longitudinal axis 624 and includes an upper channel portion 623 (identified by the ridge 623A formed on the outer surface of the housing 622 in FIG. 15). The upper channel portion 623 is defined in the chamber 694 and is radially spaced from the longitudinal axis 624.

The housing 622 further includes a slot 642 which extends for a predetermined distance therealong. The actuator 690 includes a knob 698 supported adjacent to the housing 622 and exterior of the central bore 630. The actuator 690 also includes a neck portion 700 interconnecting the knob 698 and the piston 692. The neck portion 700 extends through the slot 642.

In addition, the disposable dental prophylaxis angle 620 also includes a gear train, generally indicated at 640, which is operatively supported by the housing 622 for imparting rotational movement to the prophylaxis cup 632. The gear train 640 includes a primary drive gear 658 having a drive shaft 660 extending longitudinally within the central bore 630 and a secondary driven gear 662 in meshing engagement with the drive gear 658. The secondary, driven gear 662 is supported within the head portion 628 for rotation about an axis 664 substantially perpendicular to the longitudinal axis 624 of the housing 622. A prophylaxis cup 632 is operatively mountd to this secondary driven gear 662 in a conventional manner.

The piston 692 includes an axial passage 691 extending therethrough in a direction substantially parallel to the central bore 630. The axial passage 691 is adapted to receive and support the drive shaft 660 of the gear train 640. In addition, the gear train 640 includes a retaining clip 686 which is adapted for interference fit within the central bore 630 adjacent to the head portion 628 and serves to lock the drive gear 658 into meshing engagement with the driven gear 662. In addition, the retaining clip 686 includes an aperture 688. The drive shaft 660 is supported for rotation by the retaining clip 686 through the aperture 688 adjacent to the head portion 628 like that described in connection with the embodiments above.

The embodiment illustrated in FIGS. 15–16A differs from that disclosed in FIGS. 1–3A primarily with respect to the flow path of the dentifrice material 696 and the means by which the material 696 may be deposited on a patient's teeth. More specifically, in the embodiment disclosed in FIGS. 15–16A, the disposable prophylaxis angle 620 includes a dentifrice dispensing nipple 625 which is formed in the head portion 628 of the housing 622. The dentifrice dispensing nipple 625 is in fluid communication with the chamber 694 via the upper channel portion 623. Thus, the upper channel portion 623 is located in the housing 622 above the prophylaxis cup 632 and between the upper wall 626 of the head portion 628 and the outer raised wall 623A of the housing 622. The dentifrice dispensing nipple 625 extends parallel to the longitudinal axis 624 of the housing 622.

As best shown in FIG. 16A, the actuator 690 is manually movable in the direction of the longitudinal axis 624 of the housing 622 to move the piston 692 within the central bore 630 thereby reducing the volume of the chamber 694 to force the flowable dentifrice material 696 from the chamber 694 out the dentifrice dispensing nipple 625 via the upper channel portion 623 as illustrated in FIG. 16A.

The disposable dental prophylaxis angle of the present invention has an internal dentifrice delivery system which is manually operator-controlled to dispense the dentifrice in predetermined incremental amounts which correspond to the incremental, predetermined, indexed movement of an actuator relative to the housing of the prophy angle. Thus the speed, rate, and amount of dentifrice delivered to the prophylaxis cup is independent of the rotational speed of the gear train or any other device associated with the prophy angle. The present invention therefore provides a disposable dental prophylaxis angle having an internal dentifrice delivery system which is smoothly operated with tactile feedback to the practitioner of the position of the actuator and therefore the amount of dentifrice that is delivered to the prophy cup at any given time. The present invention provides for both the delivery of dentifrice material through the head portion of the housing to the prophy cup or to a dentifrice dispensing nipple located at the distal end of the housing and above the prophy cup. Similarly, the present invention provides for dentifrice delivery through flow passages in the primary drive gear as well as the secondary driven gear of the gear train used to operatively rotate the prophy cup.

The disposable prophy angle of the present invention is relatively small and compact and approximates the size of standard prophy angles known in the art which do not include a dentifrice delivery system. Accordingly the disposable dental prophy angle of the present invention is intuitive, easy to use and not too big or cumbersome for dental operations performed at the back of the patient's mouth.

The chamber or dental fluid reservoir of the disposable prohy angle of the present invention is also easy to charge with dentifrice material and will hold 1.0–1.25 cc of dentifrice without the need for increasing the length or circumference of the housing so as to adversely effect the dental procedures or otherwise make the use of the prophy angle counter-intuitive. The disposable prophy angle of the present invention may be individually sealed, or otherwise conveniently packaged so as to maintain the shelf-life of the dentifrice material. In addition, the prophy angle of the present invention is cost effective to manufacture and so it meets another important need that presently exists in the related art.

The invention has been described in an illustrative manner. It is to be understood that the terminology which has been used is intended to be in the nature of words of description rather than of limitation. Many modifications and variations of the invention are possible in light of the above teachings. Therefore, within the scope of the appended claims, the invention may be practiced other than as specifically described.

I claim:

1. A disposable dental prophylaxis angle comprising:
   an elongated housing defining a longitudinal axis and having a central bore and a head portion in fluid communication with said central bore;
   a prophylaxis cup rotatably supported by said head portion and in fluid communication with said central bore through said head portion;
   an actuator movably supported by said housing and including a piston cooperatively received and supported in said central bore to define a chamber of decreasable volume disposed between said piston and said head portion with flowable dentifrice material contained within said chamber;
   said actuator being manually movable in the direction of said longitudinal axis of said housing to move said piston within said central bore in an indexing fashion in successive increments of a predetermined distance therealong to reduce the volume of said chamber and to force said flowable dentifrice material in predetermined incremental amounts corresponding to the distance traveled by said piston from said chamber to said prophy cup via said head portion.

2. A disposable dental prophylaxis angle as set forth in claim 1 wherein said housing further includes a slot extending for a predetermined distance therealong;
   said actuator movably supported by said housing in the direction of said slot, said actuator including a knob supported adjacent to said housing and exterior of said central bore and a neck portion interconnecting said knob and said piston and extending through said slot.

3. A disposable dental prophylaxis angle as set forth in claim 2 wherein said neck portion cooperates with said slot to produce said successive incremental indexed movement of said piston in said central bore under the influence of a force acting on said knob.

4. A disposable dental prophylaxis angle as set forth in claim 3 wherein said slot includes a pair of opposed serrated surfaces, said neck portion including a pair of complementary surfaces cooperating with said serrated surfaces on said slot to provide successive incremental, indexed movement of said neck relative to said slot.

5. A disposable dental prophylaxis angle as set forth in claim 2 wherein said knob is moveable along said slot in a direction parallel to, but spaced from, said longitudinal axis defined by said housing, said piston including a plunger, a force stabilizing surface and a ram portion extending therebetween so as to define said piston, said force stabilizing surface extending from said neck portion in a direction so as to define an obtuse angle with said ram portion of said piston and so as to mitigate any moment force acting through said piston.

6. A disposable dental prophylaxis angle as set forth in claim 5 wherein said ram portion includes a plurality of ribs extending radially outward therefrom between said force stabilizing surface and said plunger.

7. A disposable dental prophylaxis angle as set forth in claim 5 wherein a plunger seal is mounted to said plunger and cooperates with said central bore to form a seal between said piston and said central bore at one end of said chamber.

8. A disposable dental prophylaxis angle as set forth in claim 7 wherein said housing is substantially cylindrical in the direction of said longitudinal axis and includes an upper channel portion defined in said chamber and radially spaced from said longitudinal axis, said plunger seal including a tab portion which is received in said channel portion to seal same relative to said central bore at said piston.

9. A disposable dental prophylaxis angle as set forth in claim 8 wherein said plunger includes a backing portion disposed adjacent to said tab portion of said plunger seal for supporting same as said piston is moved within said central bore to reduce the volume of said chamber.

10. A disposable dental prophylaxis angle as set forth in claim 5 further including a gear train operatively supported by said housing for imparting rotational movement to said prophylaxis cup, said gear train including a primary drive gear having a drive shaft extending longitudinally within said central bore and a secondary driven gear in meshing engagement with said drive gear and supported within said head portion for rotation about an axis substantially perpendicular to said longitudinal axis of said housing with said prophylaxis cup operatively mounted to said second driven gear.

11. A disposable dental prophylaxis angle as set forth in claim 10 wherein said piston includes an axial passage extending therethrough in a direction substantially parallel to said central bore, said axial passage adapted to receive and support said drive shaft of said gear train.

12. A disposable dental prophylaxis angle as set forth in claim 10 wherein said gear train includes a retaining clip adapted for interference fit within said central bore adjacent said head portion for locking said drive gear into meshing engagement with said driven gear.

13. A disposable dental prophylaxis angle as set forth in claim 12 wherein said retaining clip includes an aperture, said drive shaft supported for rotation by said retaining clip through said aperture adjacent said head portion.

14. A disposable dental prophylaxis angle as set forth in claim 2 wherein said housing is substantially cylindrical in the direction of said longitudinal axis and wherein said knob has an arcuate profile and extends about said cylindrical housing for a predetermined arcuate extent thereof.

15. A disposable dental prophylaxis angle as set forth in claim 2 wherein said knob has a textured surface adapted for manual manipulation by fingers and thumb.

16. A disposable dental prophylaxis angle as set forth in claim 2 wherein and said slot includes a closed distal end, said neck includes a stop surface disposed for abutting contact with said distal end of said slot to limit the longitudinal distance traveled by said piston in said central bore.

17. A disposable dental prophylaxis angle as set forth in claim 2 wherein said housing includes an open end adapted to receive the nose cone of a hand piece, an annular groove disposed about the circumference of said housing adjacent said open end and an annular collar disposed about the circumference of said housing and adapted for sliding movement in an axial direction relative to said housing, said annular collar including a lip receivable in said annular groove such that the collar extends in overlapping relationship between said housing and the hand piece and acts to stabilize said angle relative to said hand piece.

18. A disposable dental prophylaxis angle as set forth in claim 17 wherein said slot includes an open end and a closed distal end, said slot including a pair of opposed tabs spanning a portion of said slot and extending toward one another adjacent said open end, said slot adapted to receive and retain an anti-rotation nipple projecting from the hand piece with said opposed tabs coming into frictional engagement therewith.

19. A disposable dental prophylaxis angle comprising:
an elongated housing defining a longitudinal axis and having a central bore and a head portion in fluid communication with said central bore;
a prophylaxis cup rotatably supported in said head portion and in fluid communication with said central bore through said head portion;
a slot extending for a predetermined distance along said housing;
a gear train operatively supported by said housing for imparting rotational movement to said prophylaxis cup, said gear train including a primary, drive gear having a drive shaft extending longitudinally within said central bore and a secondary, driven gear in meshing engagement with said drive gear and supported within said head portion for rotation about an axis substantially perpendicular to said longitudinal axis of said housing with said prophylaxis cup operatively mounted to said secondary driven gear;
an actuator moveably supported by said housing and including a cam adapted for movement through said slot, a push rod including a cam follower and an isolation tube, said isolation tube disposed about a portion of said drive shaft along a predetermined distance of said central bore but less than the full forward extend of said drive shaft so as to present a gap between the distal end of said isolation tube and said primary drive gear, said isolation tube adapted for rectilinear movement toward and away from said drive gear relative to said drive shaft;
a piston cooperatively received within said central bore to define a chamber of decreasable volume disposed between said piston and said head portion with flowable dentifrice material contained within said chamber;
a biasing member biasing said cam follower into engagement with said cam in a direction away from said drive gear, said cam being manually pivotal about a point relative to said housing and through said slot by a force acting about said pivot point to bear against said cam follower to move said isolation tube in a direction toward said drive gear;
said piston operatively mounted to said isolation tube and adapted for movement therewith in one direction toward said drive gear, but being stationary while allowing relative movement of said isolation tube in an opposite direction away from said drive gear so as to result in movement of said piston within said central bore in an indexing fashion in successive increments of predetermined distance therealong to reduce the volume of said chamber and to force said flowable dentifrice material from said chamber to said prophylaxis cup via said head portion in predetermined incremental amounts corresponding to the distance traveled by said piston along said isolation tube.

20. A disposable dental prophylaxis angle as set forth in claim 19 further including a dam cooperatively received within said central bore and axially fixed relative to said housing, said push rod including a spring retainer, said biasing member including a coiled spring disposed about a portion of said isolation tube and between said fixed dam and said spring retainer to bias said push rod away from said drive gear.

21. A disposable dental prophylaxis angle as set forth in claim 20 wherein said dam includes an axial passage extending therethrough in a direction substantially parallel to said central bore, said axial passage adapted to receive and support said isolation tube for rectilinear movement toward and away from said drive gear.

22. A disposable dental prophylaxis angle as set forth in claim 20 wherein said spring retainer is formed integrally with said cam follower and has a lower depending leg adapted for sliding contact with said central bore and for supporting said push rod as it is moved rectilinearly within said central bore.

23. A disposable dental prophylaxis angle comprising:
an elongated housing defining a longitudinal axis and having a central bore and a head portion in fluid communication with said central bore;
a prophylaxis cup rotatably supported in said head portion and in fluid communication with said central bore through said head portion;
an actuator supported by said housing and including a piston cooperatively supported within said central bore to define a chamber of decreasable volume disposed between said piston and said head portion with flowable dentifrice material contained within said chamber;
said actuator being manually movable to move said piston within said central bore to reduce the volume of said chamber and to force said flowable dentifrice material from said chamber to said prophy cup via said head portion;
a gear train operatively supported by said housing for imparting rotational movement to said prophylaxis cup, said gear train including a primary drive gear having a drive shaft extending longitudinally within said central bore and a secondary, driven gear in meshing engagement with said drive gear and supported within said head portion for rotation about an axis substantially perpendicular to said longitudinal axis of said housing with said prophylaxis cup operatively mounted to said secondary driven gear;
said secondary, driven gear including a delivery channel extending substantially parallel to said axis of rotation thereof and in fluid communication with said prophylaxis cup and a plurality of radial connecting ports extending transverse to, and in fluid communication with, said delivery channel in said driven gear;

said drive gear including a plurality of flow paths extending through said drive gear in a direction substantially parallel to said longitudinal axis of said housing and providing fluid communication between said chamber and said radial connecting ports on said driven gear by which said flowable dentifrice may be communicated to said prophylaxis cup;

said flow paths on said drive gear being fluted such that rotation of said drive gear in one direction promotes the flow of said dentifrice material from said chamber to said radial connecting ports and such that rotation of said drive gear in an opposite direction inhibits flow of said dentifrice material from said chamber to said radial connecting ports.

24. A disposable dental prophylaxis angle as set forth in claim 23 wherein said gear train includes a 2 to 1 gear ratio between said drive gear and said driven gear.

25. A disposable dental prophylaxis angle as set forth in claim 23 wherein said gear train includes a retaining clip adapted for interference fit within said central bore adjacent said head portion for locking said drive gear into meshing engagement with said driven gear.

26. A disposable dental prophylaxis angle as set forth in claim 25 wherein said retaining clip includes an aperture, said drive shaft supported for rotation adjacent said head portion by said retaining clip through said aperture.

27. A disposable dental prophylaxis angle as set forth in claim 26 wherein said retaining clip defines a frustoconical-shaped interior surface adjacent said drive gear for directing flowable dentifrice material from said chamber to said flow paths through said drive gear.

28. A disposable dental prophylaxis angle comprising:

an elongated housing defining a longitudinal axis and having a central bore and a head portion;

a prophylaxis cup rotatably supported in said head portion;

an actuator movably supported by said housing and including a piston cooperatively received and supported within said central bore so as to defined a chamber of decreasable volume disposed between said piston and said head portion with flowable dentifrice material contained within said chamber;

said housing being substantially cylindrical in the direction of said longitudinal axis and including an upper channel portion defined in said chamber and radially spaced from said longitudinal axis;

a dentifrice dispensing nipple formed in said head portion of said housing and in fluid communication with said chamber via said upper channel portion;

said actuator being manually movable in the direction of said longitudinal axis of said housing to move said piston within said central bore to reduce the volume of said chamber and to force said flowable dentifrice material from said chamber out said dentifrice dispensing nipple via said upper channel portion.

29. A disposable dental prophylaxis angle as set forth in claim 28 wherein said upper channel portion is located in said housing above said prophylaxis cup supported in said head portion and said dentifrice dispensing nipple extends parallel to said longitudinal axis of said housing.

30. A disposable dental prophylaxis angle as set forth in claim 28 wherein said housing further includes a slot extending for a predetermined distance therealong; said actuator includes a knob supported adjacent to said housing and exterior of said central bore, and a neck portion interconnecting said knob and said piston and extending through said slot;

said actuator being manually moveable in the direction of said slot by a force acting on said knob to move said piston within said central bore in an indexing fashion in successive increments of a predetermined distance therealong to reduce the volume of said chamber and to force said flowable dentifrice material in predetermined incremental amounts corresponding to the distance traveled by said piston from said chamber out said dentifrice dispensing nipple in said head portion via said upper channel portion.

31. A disposable dental prophylaxis angle as set forth in claim 30 wherein said neck cooperates with said slot to produce said successive incremental indexed movement of said piston in said central bore under the influence of a force acting on said knob.

32. A disposable dental prophylaxis angle as set forth in claim 31 wherein said slot includes a pair of opposed serrated surfaces, said neck including a pair of complementary surfaces cooperating with said serrated surfaces on said slot to provide successive incremental, indexed movement of said neck relative to said slot.

33. A disposable dental prophylaxis angle as set forth in claim 30 wherein said knob is moveable along said slot in a direction parallel to, but spaced from, said longitudinal axis defined by said housing, said piston including a plunger, a force stabilizing surface and a ram portion extending therebetween so as to define said piston, said force stabilizing surface extending from said neck in a direction so as to define an obtuse angle with said rain portion of said piston and so as to mitigate any moment force acting through said piston.

34. A disposable dental prophylaxis angle as set forth in claim 33 wherein a plunger seal is mounted to said plunger and cooperates with said central bore to form a seal between said piston and said central bore at one end of said chamber.

35. A disposable dental prophylaxis angle as set forth in claim 34 wherein said plunger seal includes a tab portion which is received in said channel portion to seal same relative to said central bore at said piston.

36. A disposable dental prophylaxis angle as set forth in claim 35 wherein said plunger includes a backing portion disposed adjacent to said tab portion of said plunger seal for supporting same as said piston is moved within said central bore to reduce the volume of said chamber.

37. A disposable dental prophylaxis angle as set forth in claim 33 further including a gear train operatively supported by said housing for imparting rotational movement to said prophylaxis cup, said gear train including a primary drive gear having a drive shaft extending longitudinally within said central bore and a secondary driven gear in meshing engagement with said drive gear and supported within said head portion for rotation about an axis substantially perpendicular to said longitudinal axis of said housing with said prophylaxis cup operatively mounted to said second drive gear.

38. A disposable dental prophylaxis angle as set forth in claim 37 wherein said piston includes an axial passage extending therethrough in a direction substantially parallel to said central bore, said axial passage adapted to receive and support said drive shaft of said gear train.

39. A disposable dental prophylaxis angle as set forth in claim 37 wherein said gear train includes a retaining clip adapted for interference fit within said central bore adjacent said head portion for locking said drive gear into meshing engagement with said driven gear.

40. A disposable dental prophylaxis angle as set forth in claim 39 wherein said retaining clip includes an aperture, said drive shaft supported for rotation by said retaining clip through said aperture adjacent said head portion.

* * * * *